United States Patent [19]

Anhäuser et al.

[11] Patent Number: 4,587,146
[45] Date of Patent: May 6, 1986

[54] FLAT LAMINATE PART CONSISTING OF A SUBSTRATE LAYER, A COVER LAYER AND AN AUXILIARY PULL-OFF MEANS FOR THE COVER LAYER

[75] Inventors: Dieter Anhäuser, Melsbach; Gerhard Kreitlow; Hubertus Olbrich, both of Neuwied; Karl-Heinz Reinhold, Hausen; Günter Simon, Hillesheim; Karl-Heinz Gockel, Solingen-Gräfrath, all of Fed. Rep. of Germany

[73] Assignee: Lohmann GmbH & Co. KG, Neuwied, Fed. Rep. of Germany

[21] Appl. No.: 677,381

[22] Filed: Dec. 3, 1984

[30] Foreign Application Priority Data

Dec. 8, 1983 [DE] Fed. Rep. of Germany ....... 3344335

[51] Int. Cl.4 .............................. B32B 3/10; B32B 7/06
[52] U.S. Cl. ...................................... 428/41; 428/43; 428/195; 428/211; 428/220; 428/336; 428/138; 206/824
[58] Field of Search .................. 428/41, 43, 195, 217, 428/211, 220, 336, 138; 206/824

[56] References Cited

U.S. PATENT DOCUMENTS

| | | | |
|---|---|---|---|
| 2,023,829 | 12/1935 | Wright | 40/2 R |
| 2,823,673 | 2/1958 | Schladermundt et al. | D24/49 X |
| 3,221,427 | 12/1965 | Kaplan | 40/2 R |
| 3,230,649 | 1/1966 | Karn | 428/40 |
| 3,503,834 | 3/1970 | Schroter | 40/2 R X |
| 3,547,120 | 12/1970 | Grossman | D24/49 X |
| 3,639,500 | 2/1972 | Muny et al. | 428/40 |
| 3,690,999 | 4/1970 | Setzer | 428/40 |
| 3,764,447 | 10/1973 | Duff | 428/43 |
| 3,987,569 | 10/1976 | Chase | 428/41 |
| 4,264,662 | 4/1981 | Taylor et al. | 428/41 X |
| 4,397,261 | 8/1983 | Jones | 428/40 |
| 4,524,095 | 6/1985 | Gockel | 428/43 |

FOREIGN PATENT DOCUMENTS

| | | | |
|---|---|---|---|
| 238852 | 1/1960 | Australia | 40/586 |
| 2071048 | 9/1981 | United Kingdom | 40/2 R |
| 2084509 | 4/1982 | United Kingdom | 428/41 |

Primary Examiner—Alexander S. Thomas
Attorney, Agent, or Firm—Kerkam, Stowell, Kondracki & Clarke

[57] ABSTRACT

The present invention is related to a flat laminate part consisting of a substrate layer and a cover layer having an auxiliary pull-off means to so pull-off said cover layer or parts of said cover layer said auxiliary pull-off means comprising a preset cut or cuts or a preset breaking line or lines in said cover layer, said auxiliary pull-off means being improved by having a stiffened area in the surrounding of the preset cuts or preset breaking lines in order to facilitate the producing of the grasp parts for pulling off said cover layer or parts of said cover layer.

9 Claims, 6 Drawing Figures

FLAT LAMINATE PART CONSISTING OF A SUBSTRATE LAYER, A COVER LAYER AND AN AUXILIARY PULL-OFF MEANS FOR THE COVER LAYER

CROSS-REFERENCE TO RELATED PATENT

This invention is an improvement to the invention to which application Ser. No. 541,143, filed Oct. 10, 1983 is directed, which issued as U.S. Pat. No. 4,524,095 on June 18, 1985.

BACKGROUND OF THE INVENTION

The present invention is related to flat laminate parts consisting of a substrate and a cover layer with an auxiliary pull-off means for said cover layer or parts thereof.

It is often necessary to protect one or both surfaces of a flat substrate or one or both open surfaces of a flat laminate, by a cover layer before the final use thereof. Such a cover layer is necessary for instance due to the adhesive properties of said surface or its sensitivity to mechanical damage or in order to avoid evaporation of highly volatile components from a layer by way of such a surface. The cover layer in general is kept to the substrate layer by adhesive additions to said substrate layer or by the self-adhesive properties of the surface of the substrate layer which adhesive forces may be overcome by the application of mechanical pull-off forces. The problem with such compositions is to make the combination of the substrate layer and the cover layer such that both layers are securely held together but the pull-off of the cover layer or of parts thereof is easy and readily possible.

There are known already several propositions to solve this problem. Thus, a mere tearing of the laminate allows to use the finger nail to grasp a part of the cover layer and pull it off from the substrate layer and by using this part of the cover layer as grasp part to thereby allow a complete pull-off of the cover layer. It is furthermore known to compose the cover layer of several parts with a total surface larger than the surface of the substrate layer thereby producing overlapping parts in the surface of the cover layer which overlapping parts are used as grasp parts and auxiliary pull-off means in the cover layer. If no such overlapping parts are provided in the cover layer, grasp parts in the cover layer are known to be produced by sharply bending the laminate at one or several of its edges thereby causing the cover layer to be solved from the substrate layer at such edges if the cover layer is rigid enough to produce sufficient peel-off forces by such rigidity. Another known possibility to produce grasp parts for the cover layer is to cover the substrate layer by a cover layer larger than the substrate layer. Furthermore, another known means to ease the pull-off of the cover layer from the substrate layer is to produce linear cuts or preset linear breaking lines in the cover layer allowing to produce lines in the cover layer by pulling and bending the laminate wherefrom the pull-off of the cover layer may be started. Still furthermore, it is known to incorporate into the laminate a wire or a strap between the cover layer and the substrate layer said wire or strap projecting over the edges of the laminate which wire or strap serves as an auxiliary pull-off means for the cover layer from the substrate layer. It is furthermore known a flat laminate part consisting of a substrate layer and a cover layer the adhesive forces between said substrate layer and said cover layer being such that both layers are securely held together, but a pull-off of said cover layer is readily possible by hand or mechanically, said flat laminate part having additionally an auxiliary pull-off means to so pull-off said cover layer or parts of said cover layer by hand or mechanically said auxiliary pull-off means comprising preset cuts or breaking lines in the cover layer, wherein said preset cuts or preset breaking lines in said cover layer are positioned and formed such that there is at least one part of the cover layer which can be grasped per each part of said cover layer to be pulled off, said grasp part getting exposed by bending the flat laminate part to form a concave curvature of the surface of said cover layer opposite to the surface of said cover layer adhearing to said substrate layer, the at least two points of attack of the force producing such bending of the flat laminate part being distributed over the surface of the flat laminate part such that the forces acting substantially vertically from the laminate in the bend, result in a peeling off of said grasp part of said cover layer.

All these proposals to solve the problem are not satisfactory because they either necessitate additional material or complicated procedures to produce them or only give a sufficient large grasp part to easily pull-off the cover layer from the adhearing substrate layer if there is a sufficient difference in the stiffness of the cover layer and of the substrate layer.

SUMMARY OF THE INVENTION

It is therefore an object of the present invention to provide an auxiliary pull-off means for the cover layer or parts thereof in such flat laminate parts which avoid the above mentioned disadvantages.

According to the present invention the solution of this object is a flat laminate part consisting of a substrate layer and a cover layer, the adhesive forces between the substrate layer and the cover layer being such that both the substrate layer and the cover layer are securely held together, but a pull-off of the cover layer from the substrate layer is readily possible, said flat laminate having an auxiliary pull-off means to so pull-off the cover layer or parts thereof along preset cuts or preset breaking lines in the cover layer, the preset cuts or preset breaking lines being particularly positioned and formed such that there is at least one part of the cover layer which can be grasped, for each part of the cover layer to be pulled off, which part is getting exposed by bending the flat laminate part to form a concave curvature of the surface of the cover layer opposite to the surface of the cover layer adhearing to the substrate layer with the at least two points of attack of the force producing such bending of the flat laminate part being distributed over the surface of the flat laminate part such that the mechanical forces acting substantially vertically to the laminate result in a peeling off of the grasp parts of the cover layer characterized in that there is provided a stiffened area surrounding said preset cuts or preset breaking lines to ease the peeling off of said grasp parts from said cover layer to pull-off said cover layer or parts thereof.

BRIEF DESCRIPTION OF THE DRAWINGS

The invention is further illustrated by means of the attached drawings without however limiting the same thereto.

DETAILED DESCRIPTION

Figure 1:
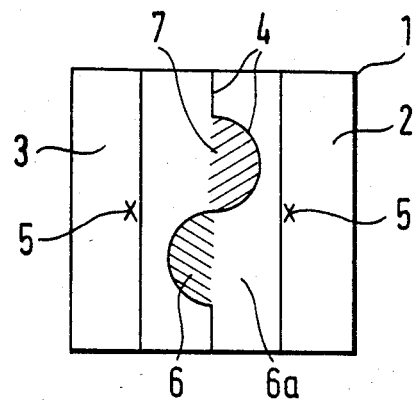
FIG. 1 shows a top view of the cover layer of a quadrangular part of the flat laminate according to the present invention.
Figure 2:
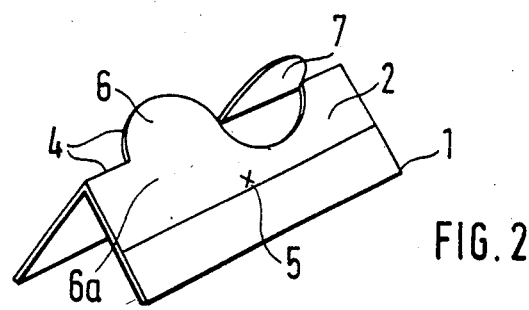
FIG. 2 shows a perspective view of the bent laminate part of FIG. 1.

In FIG. 1, (1) is the quadrangular laminate part as such. The cover layer of this laminate part is subdivided by the preset cut or preset breaking line (4) into two partial surface areas (2) and (3). The preset cut or preset breaking line (4) runs from one edge of the laminate part to the opposite edge thereof and partially has the form of a sinusoid (sine curve). This sine curve defines the hatched or shaded surface area (6) as grasp or pick-up part for the partial surface area (2) of the cover layer and the hatched area (7) as grasp part of the partial surface area (3) of the cover layer. The stiffened area (6a) on the part (2) and an equal area on the part (3) cover the whole area of breaking line (4) and is somewhat larger. The crosses (5) characterize those areas, wherein the forces producing the bending of the laminate and thereby producing the exposition of the grasp parts (6) and (7), are to be applied. Or, the laminate is bent substantially along a line connecting the end points of line (4) at the opposite edges of the laminate to produce the peel-off of the grasp parts (6) and (7). A perspective illustration of the bent quadrangular laminate part is given in FIG. 2. The numbers contained therein have the same meaning as in FIG. 1. The exposed grasp parts (6) and (7) are readily recognizable and show that the pull-off of the surface areas (2) and (3) by hand or mechanically is readily possible.

Figure 3:
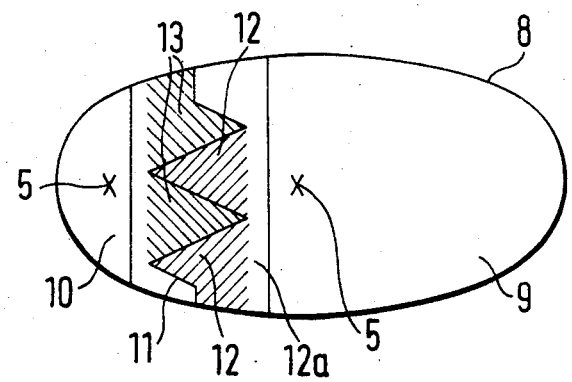
FIGS. 3 to 6 show the top view of the cover layers of other embodiments of the flat laminate part according to the present invention.

FIG. 3 shows an oval-shaped embodiment (8) of a laminate part according to the present invention. The cover layer thereof is subdivided asymmetrically by a preset cut or preset breaking line (11) in the partial surface areas (9) and (10) different in surface area from each other. The preset cut or preset breaking line (11) connects two opposite points at the edge of the oval and is zigzag formed and produces the hatched surface area (12) as grasp part for the partial surface area (9) and the hatched area (13) as grasp part for the partial surface area (10). The zigzag form actually shown in FIG. 3 may of course also be a mirror inversion which is true for many preset cut or, respectively, preset breaking line embodiments shown in the present Figures. If bending forces in FIG. 3 attack in the area defined with crosses (5), the grasp parts (12) and (13) are exposed and the partial or complete pull-off of the cover layer is readily possible.

Figure 4:
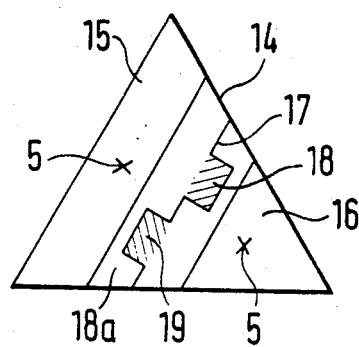

A triangular-shaped embodiment (14) of the laminate part according to the present invention is shown in FIG. 4. In this embodiment the present cut or, respectively, breaking line (17) runs from one edge of the triangular to one of the other edges thus subdividing the surface of the cover layer into the partial surface areas (15) and (16) different in surface size. The grasp parts (18) and (19) of this embodiment have a rectangular shape and become exposed upon the application of bending forces in the areas (5). The partial or complete pull-off of the cover layer may then occur by hand or mechanically.

Figure 5:
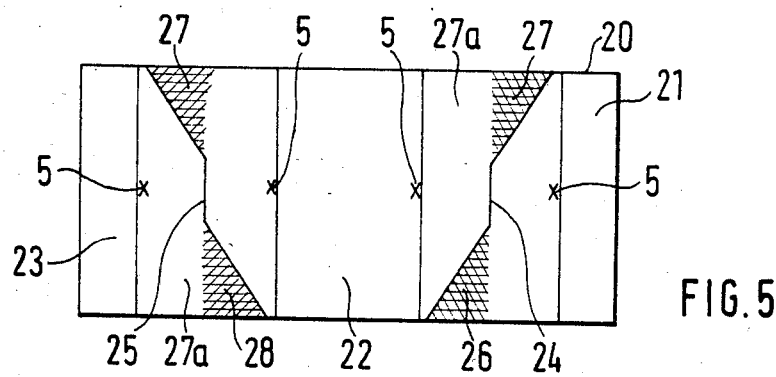

A further embodiment of the present invention is shown in FIG. 5. In this embodiment two preset cuts or breaking lines subdivide the surface of the cover layer of the laminate part (20) in three partial surface areas (21), (22) and (23). The preset cuts or breaking lines run from one of the longer edges of the rectangular shape to the other long side. The preset cuts or preset breaking lines are shaped angled such that the triangular grasp part (26) for the one outer surface area part (21), the triangular grasp part (27) for the middle partial area (22) and the grasp part (28) for the other outer partial surface area (23) is formed. The exposition of these grasp parts occurs after allowing bending forces to attack in the areas indicated with crosses (5). The exposed grasp parts (26), (27) and (28) readily allow the partial or complete pull-off of the cover layer.

Figure 6:
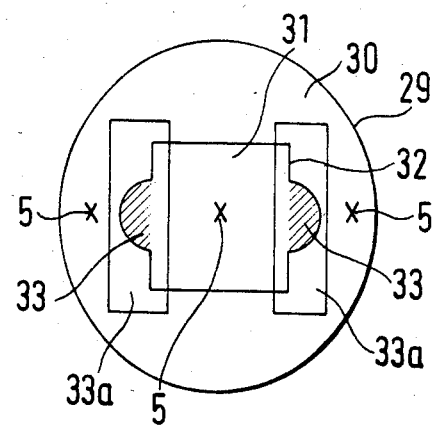

The circular or round embodiment (29) of the laminate part according to the present invention as shown in FIG. 6 has the particularity that the preset cut or preset breaking line (32) is a closed line, has the geometrical form substantially of an equilateral square and does not touch any edge of this embodiment of the laminate part. In order to pull off that partial surface area (31) embraced by the preset cut or breaking line partially from the cover layer allowing the partial surface area (31) to leave the partial surface area (30), the preset substantially equilaterally quadrangular cut or breaking line has two convexities at two opposite edges of the equilateral square projecting into the partial surface areas (30). These convexities (33) represent the grasp parts and may be exposed by the application of bending forces in the areas (5). The partial surface area (31) has two grasp parts (33) and thereby may be readily pulled off.

The Examples illustrated in the present drawings indicate that the present invention may have many various embodiments and is only limited by the definitions given in the following claims. Thus, a prerequisite of the present invention is that the cover layer is subdivided by the preset cuts or preset breaking lines in at least two partial surface areas. The preset cuts or breaking lines connect two points at the edge of the laminate part or form closed geometrical figures which do not touch any edge of the laminate part. The latter embodiment is in particular useful in connection with the pull-off of partial surface areas positioned within the total surface area.

The cover layer and/or the substrate layer may be composed of one or a multitude of individual layers. In all cases where there are particular circumstances, which prevent that the difference in the stiffness of the cover layer and that of the substrate layer is not sufficiently large in order to peel off the grasp part by bending the flat laminate part the area with increased stiffness in the surrounding of the preset cuts or preset breaking lines in accordance with the present invention gives a solution of the problem. The area of increased stiffness is flat in itself, having a thickness of 30 to 150 μm and its form depends upon the form of the preset cuts or preset breaking lines. They have to cover at least the area of the preset cut or preset breaking line (see the present Figures).

The stiffened area may be produced by known methods. Thus, it may be produced by a liquid, dissolved or emulgated phase directly upon the cover layer before the formation of the preset cut or preset breaking line. More particularly, the stiffened area may be produced immediately on the cover layer by cooling a liquid substrate layer. Another technique is evaporating the solvent of a dissolved substrate. Yet another technique is evaporation of the emulsifying solvent of an emulgated substrate.

Another preferred method consists in producing the area of of higher stiffness by applying another layer in the form of single-sided adhesive material of necessary thickness. Also in this embodiment, the preset cuts or preset breaking lines are produced after such material has been applied.

The partial or complete pull-off of the cover layer rendered possible by the present invention exposes the second surface of the substrate or a part thereof such that it may be used for the subsequent purpose of use of the substrate. In a preferred embodiment of the present invention, this surface of the substrate is self-adhesive such that the substrate or parts thereof, after removal of the cover layer, may be fixed to an intended base. The outer edge or contour of the laminate part may be varied and depends upon the necessities of the intended use thereof. The substrate may also have a cover layer on both of its surfaces. In accordance with the present invention, in this embodiment there may be provided preset cuts or preset breaking lines in both cover layers which allows the removal of one or both cover layers simultaneously or at different times.

The preset cuts or preset breaking lines in the cover layer may be produced by methods known to the expert in the art, for instance by punching, cutting, pressing, squeezing, or stamping while the preset beaking lines are preferably produced by perforation, local chemical treatment or by the application of pull-off wires.

What we claim is:

1. A flat laminate part comprising:
a flexible substrate layer having at least one surface;
a cover layer at least partially on the one surface of said substrate layer;
means for effecting adhesion of said cover layer to said surface of the substrate layer in the area of said cover layer such that the layers are securely held together but may be pulled apart;
a substantially continuous cut or preset breaking line in said cover layer from one edge to another edge of said cover layer thereby separating the cover layer into two parts, at least parts of said cut or preset breaking line respectively diverting substantially from a straight connection line between the end points of the cut at the edges of the cover layer into each part of said cover layer to define the locations of grasp parts; and
stiffened areas in said cover layer surrounding said cut or preset breaking line and including at least the grasp part locations defined within said diverting parts of said cut or preset breaking line;
the stiffness of said stiffened areas and the adhesion between said substrate layer and said cover layer being such that, upon bending of the flat laminate part substantially along said straight connection line between the end points of said cut at the edges of said cover layer in a direction which produces a convex curvature of the exposed surface convexly on the side of the cover layer, said diverting parts of said cut or preset breaking line into each part of the cover layer are separated and peeled off from the substrate layer to thereby expose the grasp parts.

2. A flat laminate part in accordance with claim 1, wherein said stiffened areas comprise another layer of single-sided adhesive material such that the total thickness of said stiffened areas is from 30 to 150 μm.

3. A flat laminate part in accordance with claim 1, wherein said stiffened areas are formed immediately on said cover layer by cooling a liquid substrate layer.

4. A flat laminate part in accordance with claim 1 wherein said stiffened areas are formed directly on said cover layer by evaporating the solvent of a dissolved substrate.

5. A flat laminate part in accordance with claim 1, wherein said stiffened areas are formed directly on said cover layer by evaporation of the emulsifying of an emulgated substrate.

6. A flat laminate part in accordance with claim 1, wherein at least one of said cover and substrate layers in turn comprises a plurality of layers.

7. A flat laminate part in accordance with claim 1 wherein said substantially continuous cut or preset breaking line extends from one edge to an opposite edge of said cover layer.

8. A flat laminate part in accordance with claim 1, which further comprises:
a second cover layer on a second surface of said substrate layer opposite to the surface with the first cover layer;
means for effecting adhesion of said second cover layer to said opposite surface of the substrate layer in the area of said second cover layer such that the layers are securely held together but may be pulled apart;
a substantially continuous cut or preset breaking line in said second cover layer from edge to another edge of said second cover layer separating said second cover layer into two parts, at least parts of said cut in said second cover layer respectively diverting substantially from a straight connection line between the end points of the cut at the edges of said second cover layer into each part of said second cover layer to define the locations of grasp parts for said second cover layer;
stiffened areas in said second cover layer surrounding said cut or preset breaking line in said second cover layer and including at least the locations defined within said diverting parts of said cut or preset breaking line;
the stiffness of said stiffened areas in said second cover layer and the adhesion between said substrate layer and said second cover layer being such that, upon bending of the flat laminate part substantially along said straight connection line between the end points of said cut at the edges of said second cover in a direction which produces a convex curvature of the exposed surface of said second cover layer, said diverting parts of said cut line into each part of the second cover layer are separated and peeled off from the substrate layer to thereby expose the grasp parts.

9. A flat laminate part comprising:
a flexible substrate having at least one surface;
a cover layer at least partially on the one surface of said substrate layer;
means for effecting adhesion of said cover layer to said surface of the substrate layer in the area of said cover layer such that the layers are securely held together but may be pulled apart;
a substantially continuous cut or preset breaking line in said cover layer representing a closed geometrical form not touching any edge of said cover layer, portions of said cut or preset breaking line being formed as projections to define the locations of grasp parts;

stiffened areas in said cover layer surrounding said portions of said cut or preset breaking line and including at least the defined grasp part locations;

the stiffness of said stiffened areas and the adhesion between said substrate layer and said cover layer being such, that upon bending of the flat laminate part substantially along a side of the closed geometrical form in a direction which produces a convex curvature of the exposed surface of the cover layer, the grasp part portions of said closed form are separated and peeled off from the substrate layer and thus exposed.

* * * * *